(12) United States Patent
Henke et al.

(10) Patent No.: US 8,147,420 B2
(45) Date of Patent: Apr. 3, 2012

(54) RESPIRATORY AIR TEMPERATURE AND PRESSURE SENSOR

(75) Inventors: Reinhold Henke, Plymouth, MN (US); Evan Stuart Johnston, Blaine, MN (US); Alan Bradley Jones, Maple Grove, MN (US)

(73) Assignee: Dymedix Corporation, Shoreview, MN (US)

( * ) Notice: Subject to any disclaimer, the term of this patent is extended or adjusted under 35 U.S.C. 154(b) by 341 days.

(21) Appl. No.: 12/491,068

(22) Filed: Jun. 24, 2009

(65) Prior Publication Data

US 2009/0318781 A1   Dec. 24, 2009

Related U.S. Application Data

(60) Provisional application No. 61/075,136, filed on Jun. 24, 2008.

(51) Int. Cl.
*A61B 5/087* (2006.01)
(52) U.S. Cl. ........................................ 600/538; 600/529
(58) Field of Classification Search .................. 600/529, 600/538–542
See application file for complete search history.

(56) References Cited

U.S. PATENT DOCUMENTS

| 5,311,875 | A | 5/1994 | Stasz |
| D410,584 | S | 6/1999 | Stasz |
| D417,161 | S | 11/1999 | Stasz |
| 6,485,432 | B1 * | 11/2002 | Stasz et al. ..................... 600/532 |
| 6,551,256 | B1 | 4/2003 | Stasz |
| 6,702,755 | B1 | 3/2004 | Stasz |
| 6,894,427 | B2 | 5/2005 | Alfini |
| 2003/0199780 | A1 * | 10/2003 | Page ............................. 600/538 |
| 2006/0270941 | A1 * | 11/2006 | Xie et al. ....................... 600/529 |
| 2008/0146955 | A1 * | 6/2008 | Horii et al. .................... 600/529 |

FOREIGN PATENT DOCUMENTS

WO   WO 9705824 A1 * 2/1997
WO   WO 2009/158425 A1 * 12/2009

* cited by examiner

*Primary Examiner* — Miranda Le
*Assistant Examiner* — Meredith Weare
(74) *Attorney, Agent, or Firm* — Nikolai & Mersereau, P.A.; Thomas J. Nikolai

(57) ABSTRACT

An apparatus and method can be configured to detect respiratory air temperature information and respiratory air pressure information from a patient using a first piezoelectric film and a second piezoelectric film, wherein at least a portion of the second piezoelectric film overlaps at least a portion of the first piezoelectric film. In an example, the first and second piezoelectric films can be sized and shaped to be disposed on an upper lip of a subject. In certain examples, the first piezoelectric film can include a non-overlap portion exposed to nasal respiration, and the second piezoelectric film can include a non-overlap portion exposed to oral respiration.

20 Claims, 7 Drawing Sheets

RESPIRATORY AIR TEMPERATURE AND PRESSURE SENSOR

CLAIM OF PRIORITY

This patent application claims the benefit of priority to U.S. Provisional Patent Application Ser. No. 61/075,136, filed on Jun. 24, 2008, which application is herein incorporated by reference in its entirety.

TECHNICAL FIELD

This invention relates generally to the field of electronic sensors and more specifically to the area of diagnosing patients who suffer from sleep disorders. More particularly, the present invention relates to a polarized respiratory air temperature and pressure change sensor for diagnosing sleep disorders in sleep laboratory patients.

BACKGROUND

In addressing sleep related problems, such as sleep apnea, insomnia and other physiologic events or conditions occurring during sleep, various hospitals and clinics have established laboratories, sometimes referred to as "Sleep Laboratories" (sleep labs). At these sleep labs, using instrumentation, such as patient bio-data sensors connected to a polysomnograph (PSG) machine, a patient's sleep patterns may be monitored and recorded for later analysis so that a proper diagnosis may be made and a therapy prescribed. Varieties of sensors have been devised for providing recordable signals related to respiratory (inhaling and exhaling) patterns during sleep. These sensors commonly are mechanical to electrical transducers that produce an electrical signal related to respiration.

The current sleep lab accreditation guidelines, as per the American Academy of Sleep Medicine (AASM), use two different sensing systems at the same time on the same patient to measure respiratory air temperature and respiratory air pressure changes. Respiratory air temperature fluctuations (changes) can be measured using either a thermocouple or a thermistor attached directly to a sleep lab's PSG machine. Respiratory air pressure fluctuations (changes) are can be measured using a nasal pressure prong cannula placed in the patient's nostrils and attached, via a plastic hose, to an air pressure transducer. The output of air pressure transducer connects directly to the PSG machine.

Air pressure transducers with nasal cannulas in combination with either a thermistor or thermocouple, as used in sleep studies, are invasive, uncomfortable and prone to clogging and body movement and, thus, put an unnecessary strain and discomfort on patients.

SUMMARY

The present inventors have recognized, among other things, there is a need to provide a polarized respiratory air temperature and pressure change sensing method that does not require the patient to wear both a temperature sensor and a separate pressure sensor at the same time.

Furthermore, there is a need to provide a polarized respiratory air temperature and pressure change sensor, which indicates, via the output polarity of its signal wire pair, that the respiratory air temperature and pressure changes are the result of either inspired or expired air movement.

Furthermore, there is a need for a polarized respiratory air temperature and pressure change sensor that employs two independent polyvinylidene fluoride (PVDF) film transducers in a sandwiched arrangement in order to provide a rigid phase and polarity relationship between respiratory air temperature and respiratory air pressure changes to final graphical indication of the individually processed PVDF film transducers signals on a PSG machine display.

Furthermore, there is a need to provide a single polarized respiratory air temperature and pressure change sensor capable of detecting oral respiratory air temperature and pressure changes and nasal respiratory air temperature and pressure changes at the same time using the same sensor.

Furthermore, there is a need to provide a single polarized respiratory air temperature and pressure change sensor using two independent PVDF film transducers in a single sensor to afford the sleep professional with a simpler method for diagnosing sleep related disorders.

Furthermore, there is also a need to provide a polarized respiratory air temperature and pressure change sensor capable of using two independent polarized piezoelectric film sensors to thereby yield a rigid phase relationship between respiratory air flow (inspiration and expiration) to final graphical indication of the polarized piezoelectric film sensor signals on PSG machine display.

The present inventors have recognized, among other things, that a sensor can be provided to simultaneously detect both respiratory air temperature changes and respiratory air pressure changes.

In certain examples, a sensor can be provided for monitoring respiratory air temperature and pressure changes using two PVDF film transducers. The construction of such sensors more readily allow the temperature signal to be separated from the pressure signal using conventional signal processing techniques (filtering) in a way that preserves the appropriate phase relationship between the temperature and pressure excursions detected by the sensors.

In various examples, the sensor generates a separate polarized respiratory air temperature change signal output and a separate polarized respiratory air pressure change signal output using two PVDF film transducers in a sandwich type construction, which make up the polarized respiratory air temperature and pressure change sensor.

The polarized respiratory air temperature and pressure change sensor connects to a PSG machine, via an attached respiratory air temperature and pressure change transducer signal processing apparatus described the commonly-assigned Peter Stasz U.S. Provisional Application 61/075,124, entitled "Apparatus and Method for Processing Respiratory Air Temperature and Pressure Change Transducer Signals", filed Jun. 24, 2008, incorporated herein in its entirety, to provide a sleep disorder-diagnosing professional with both the respiratory temperature and pressure waveforms at the same time from the same sensor indicating whether a sleeping patient is breathing normally or breathing abnormally.

In an example, a polarized respiratory air temperature and pressure change sensor for use in sleep monitoring equipment comprises two differently shaped and sandwiched PVDF film transducers. In some examples, the sensor includes two differently shaped PVDF films overlaying each other but separated by an energy buffering layer to form a sensor having two PVDF film transducers each with a substantial non-overlapped PVDF film area. One PVDF film transducer responds more to thermal energy (temperature) and the other PVDF film transducer responds more to the kinetic energy (pressure) of the inhaled or exhaled air molecules to the point where the pyroelectric signal (temperature) can more readily be isolated from the piezoelectric signal (pressure) using conventional signal processing techniques.

In Example 1, an apparatus for simultaneously detecting respiratory air temperature information and respiratory air pressure information from a patient, the apparatus includes a respiratory air temperature piezoelectric film sensor configured to detect respiratory air temperature information, and a respiratory air pressure piezoelectric film sensor configured to detect respiratory air pressure information, wherein at least a portion of the respiratory air temperature piezoelectric film sensor overlaps at least a portion of the respiratory air pressure piezoelectric film sensor, each of the respiratory air temperature piezoelectric film sensor and the respiratory air pressure piezoelectric film sensor including a non-overlap portion, the non-overlap portion of the respiratory air temperature piezoelectric film sensor proximate a first end of the apparatus, and the non-overlap portion of the respiratory air pressure piezoelectric film sensor proximate a second end of the apparatus, the second end substantially opposite to the first end.

In Example 2, the respiratory air temperature piezoelectric film sensor and the respiratory air pressure piezoelectric film sensor of Example 1 are optionally included in a single sensor apparatus sized and shaped to be disposed on an upper lip of the patient.

In Example 3, the first end of the apparatus of any one or more of Examples 1-2 is optionally exposed to nasal respiratory air flow and the second end of the apparatus of any one or more of Examples 1-2 is optionally exposed to oral respiratory air flow.

In Example 4, the respiratory air temperature piezoelectric film sensor of any one or more of Examples 1-3 optionally includes a respiratory air temperature polyvinylidene fluoride (PVDF) film sensor and the respiratory air pressure piezoelectric film sensor of any one or more of Examples 1-3 optionally includes a respiratory air pressure PVDF film sensor.

In Example 5, each of the respiratory air temperature piezoelectric film sensor and the respiratory air pressure piezoelectric film sensor of any one or more of Examples 1-4 optionally include a first major surface and a second major surface, wherein the respiratory air temperature piezoelectric film sensor of any one or more of Examples 1-4 optionally includes a first electrode coupled to a the first major surface and a second electrode coupled to the second major surface, and the respiratory air pressure piezoelectric film sensor of any one or more of Examples 1-4 optionally includes a first electrode coupled to the first major surface and a second electrode coupled to the second major surface.

In Example 6, the first electrode of the respiratory air temperature piezoelectric film sensor of Example 5 is optionally bonded to the first major surface of the respiratory air temperature piezoelectric film sensor using a conductive adhesive, wherein the second electrode of the respiratory air temperature piezoelectric film sensor of Example 5 is optionally bonded to the second major surface of the respiratory air temperature piezoelectric film sensor using a conductive adhesive, wherein the first electrode of the respiratory air pressure piezoelectric film sensor of Example 5 is optionally bonded to the first major surface of the respiratory air pressure piezoelectric film sensor using a conductive adhesive, and wherein the second electrode of the respiratory air pressure piezoelectric film sensor of Example 5 is optionally bonded to the second major surface of the respiratory air pressure piezoelectric film sensor using a conductive adhesive.

In Example 7, the apparatus of any one or more of Examples 1-6 optionally includes a first exterior layer overlying a first major surface of the respiratory air temperature piezoelectric film sensor opposite the respiratory air pressure piezoelectric film sensor, and a second exterior layer overlying a first major surface of the respiratory air pressure piezoelectric film sensor opposite the respiratory air temperature piezoelectric film sensor.

In Example 8, the apparatus of any one or more of Examples 1-7 optionally include a double sided adhesive tape layer disposed between the respiratory air temperature piezoelectric film sensor and the respiratory air pressure piezoelectric film sensor, the double sided adhesive tape layer configured to couple the respiratory air temperature piezoelectric film sensor to the respiratory air pressure piezoelectric film sensor and to isolate the respiratory air temperature piezoelectric film sensor from the respiratory air pressure piezoelectric film sensor.

In Example 9, the non-overlap portion of the respiratory air temperature piezoelectric film sensor of any one or more of Examples 1-8 is optionally configured to be exposed to nasal respiration.

In Example 10, the non-overlap portion of the respiratory air pressure piezoelectric film sensor of any one or more of Examples 1-9 is optionally configured to be exposed to oral respiration.

In example 11, the respiratory air temperature piezoelectric film sensor of any one or more of Examples 1-10 is optionally configured to provide information indicative of respiratory air temperature to an electronic signal processing circuit, the electronic signal processing circuit configured to produce a first signal output indicative of respiratory air temperature, and the respiratory air pressure piezoelectric film sensor of any one or more of Examples 1-10 is optionally configured to provide information indicative of respiratory air pressure to an electronic signal processing circuit, the electronic signal processing circuit configured to produce a second signal output indicative of respiratory air pressure.

In Example 12, the respiratory air temperature piezoelectric film sensor and the respiratory air pressure piezoelectric film sensor of any one or more of Examples 1-11 are optionally configured to provide a rigid phase and polarity relationship between respiratory air temperature and respiratory air pressure.

In Example 13, a system includes a polarized respiratory air temperature and pressure piezoelectric film sensor, sized and shaped to be disposed on an upper lip of a patient, the polarized respiratory air temperature and pressure piezoelectric film sensor configured to receive oral and nasal respiration and to provide information indicative of respiratory air temperature and information indicative of respiratory air pressure to an electronic signal processing circuit, the polarized respiratory air temperature and pressure piezoelectric film sensor including a respiratory air temperature piezoelectric film sensor configured to detect respiratory air temperature information, a respiratory air pressure piezoelectric film sensor configured to detect respiratory air pressure information, wherein at least a portion of the respiratory air temperature piezoelectric film sensor overlaps at least a portion of the respiratory air pressure piezoelectric film sensor, each of the respiratory air temperature piezoelectric film sensor and the respiratory air pressure piezoelectric film sensor including a non-overlap portion, the non-overlap portion of the respiratory air temperature piezoelectric film sensor proximate a first end of the apparatus, and the non-overlap portion of the respiratory air pressure piezoelectric film sensor proximate a second end of the apparatus, the second end substantially opposite to the first end, and wherein the non-overlap portion of the respiratory air temperature piezoelectric film sensor is configured to be exposed to nasal respiration, and the non-overlap portion of the respiratory air pressure piezoelectric film sensor is configured to be exposed to oral respiration, an electronic signal processing circuit configured to receive the information indicative of a respiratory air temperature and information indicative of a respiratory air pressure from the polarized respiratory air temperature and pressure piezoelectric film sensor, wherein the electronic signal processing circuit is configured to simultaneously process the received respiratory air temperature information and the received respiratory air pressure information to produce a first signal output indicative of respiratory air temperature and a second signal output indicative of respiratory air pressure, and a polysomnograph machine configured to receive the first signal output and the second signal output from the electronic signal processing circuit and to display the received respiratory air temperature information and the received respiratory air pressure information.

In Example 14, a method for simultaneously detecting respiratory air temperature information and respiratory air pressure information from a patient using an apparatus includes detecting respiratory air temperature information using a respiratory air temperature sensor including a first piezoelectric film, and detecting respiratory air pressure information using a respiratory air pressure sensor including a second piezoelectric film, at least a portion of the second piezoelectric film overlapping at least a portion of the first piezoelectric film, wherein the first piezoelectric film includes a first non-overlap portion proximate a first end of the apparatus and the second piezoelectric film includes a second non-overlap portion proximate a second end of the apparatus, the second end substantially opposite to the first end.

In Example 15, the method of Example 14 optionally includes exposing the non-overlap portion of the first piezoelectric film sensor to nasal respiration, and exposing the non-overlap portion of the second piezoelectric film sensor to oral respiration.

In Example 16, the detecting respiratory air temperature information and the detecting respiratory air pressure information of any one or more of Examples 14-15 optionally include using a single sensor apparatus sized and shaped to be disposed on an upper lip of the patient, the single sensor apparatus including the first piezoelectric film and the second piezoelectric film, wherein the first end of the apparatus is exposed to nasal respiratory air flow and the second end of the apparatus is exposed to oral respiratory air flow.

In Example 17, the detecting respiratory air temperature information of any one or more of Examples 14-16 optionally includes using a first polyvinylidene fluoride (PVDF) film, wherein the detecting respiratory air pressure information includes using a second PVDF film.

In Example 18, the method of any one or more of Examples 14-17 optionally include providing information indicative of respiratory air temperature to an electronic signal processing circuit, the electronic signal processing circuit configured to produce a first signal output indicative of respiratory air temperature, and providing information indicative of respiratory air pressure to an electronic signal processing circuit, the electronic signal processing circuit configured to produce a second signal output indicative of respiratory air pressure.

In Example 19, the providing the information indicative of respiratory air temperature and respiratory air pressure of Example 18 optionally includes providing a rigid phase and polarity relationship between respiratory air temperature and respiratory air pressure.

In Example 20, the providing the information indicative of respiratory air temperature of any one or more of Examples 18-19 optionally includes using a first electrode coupled to a first major surface of first piezoelectric film and a second electrode coupled to a second major surface of the first piezoelectric film, and the providing the information indicative of respiratory air pressure of any one or more of Examples 18-19 optionally includes using a first electrode coupled to a first major surface of the second piezoelectric film and a second electrode coupled to a second major surface of the second piezoelectric film.

Further areas of applicability of the present invention will become apparent from the description provided herein. It should be understood that the description and specific examples are intended for purposes of illustration only and are not intended to limit the scope of the present disclosure.

DESCRIPTION OF THE DRAWINGS

The drawings described herein are for illustration purposes only and are not intended to limit the scope of the present disclosure in any way.

The forgoing features, objects and advantages of the invention will become apparent to those skilled in the art from the following detailed description of a preferred embodiment, especially when considered in conjunction with the accompanying drawings in which like the numerals in the several views refer to the corresponding parts.

DESCRIPTION OF THE DRAWINGS

The following description is merely exemplary in nature and is not intended to limit the present disclosure, applications or uses.

Figure 1:
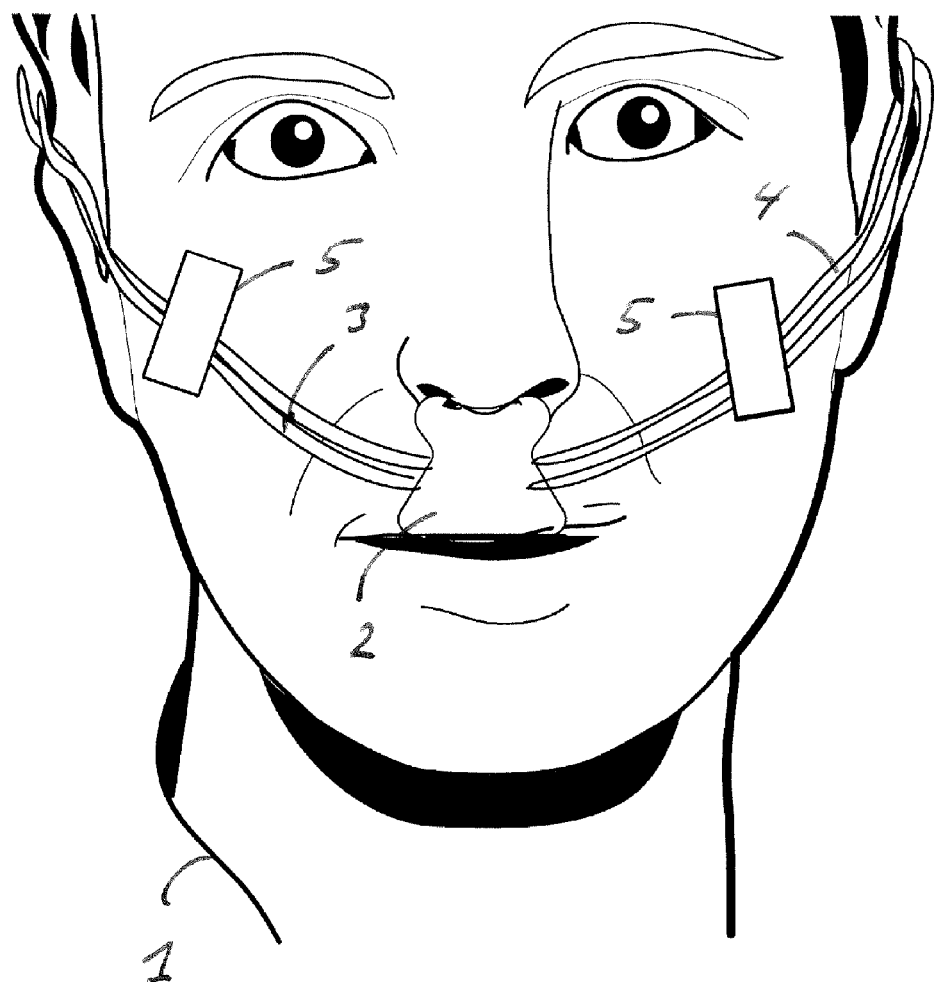
FIGS. 1-2 illustrate generally an example of a sensor affixed to a patient for sensing respiratory air temperature change and respiratory air pressure change.

FIG. 1 illustrates generally an example of a sensor affixed to a patient for sensing respiratory air temperature change and respiratory air pressure change. Referring to FIG. 1, there is indicated generally by numeral 1 a typical sleep laboratory patient who has been outfitted with a temperature and pressure sensor 2 especially designed for use with a PSG in a sleep lab setting. A pair of temperature output wires 3 and a pair of pressure output wires 4 are secured to the face of a sleep lab patient 1 using strips of adhesive medical tape 5 as indicated.

Figure 2:
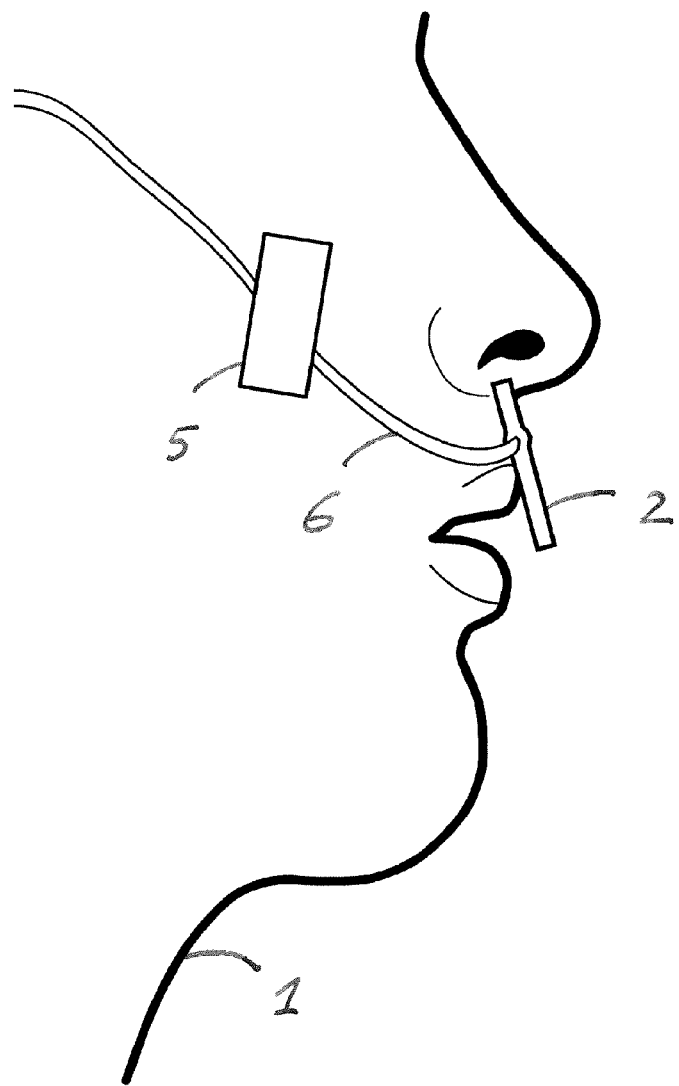

FIG. 2 illustrates generally an example of a sensor affixed to a patient for sensing respiratory air temperature change and respiratory air pressure change. Referring to FIG. 2, there is shown a side view of the sleep laboratory patient 1 who has been outfitted with a temperature and pressure sensor 2. A pair of output wires 6 is secured to the face of a sleep lab patient 1 using a strip of adhesive medical tape 5 as indicated.

Having described the overall configuration of the temperature and pressure sensor with the aid of FIGS. 1 and 2, a more detailed explanation of a specific implementation of the temperature and pressure sensor will now be presented.

Figure 3:
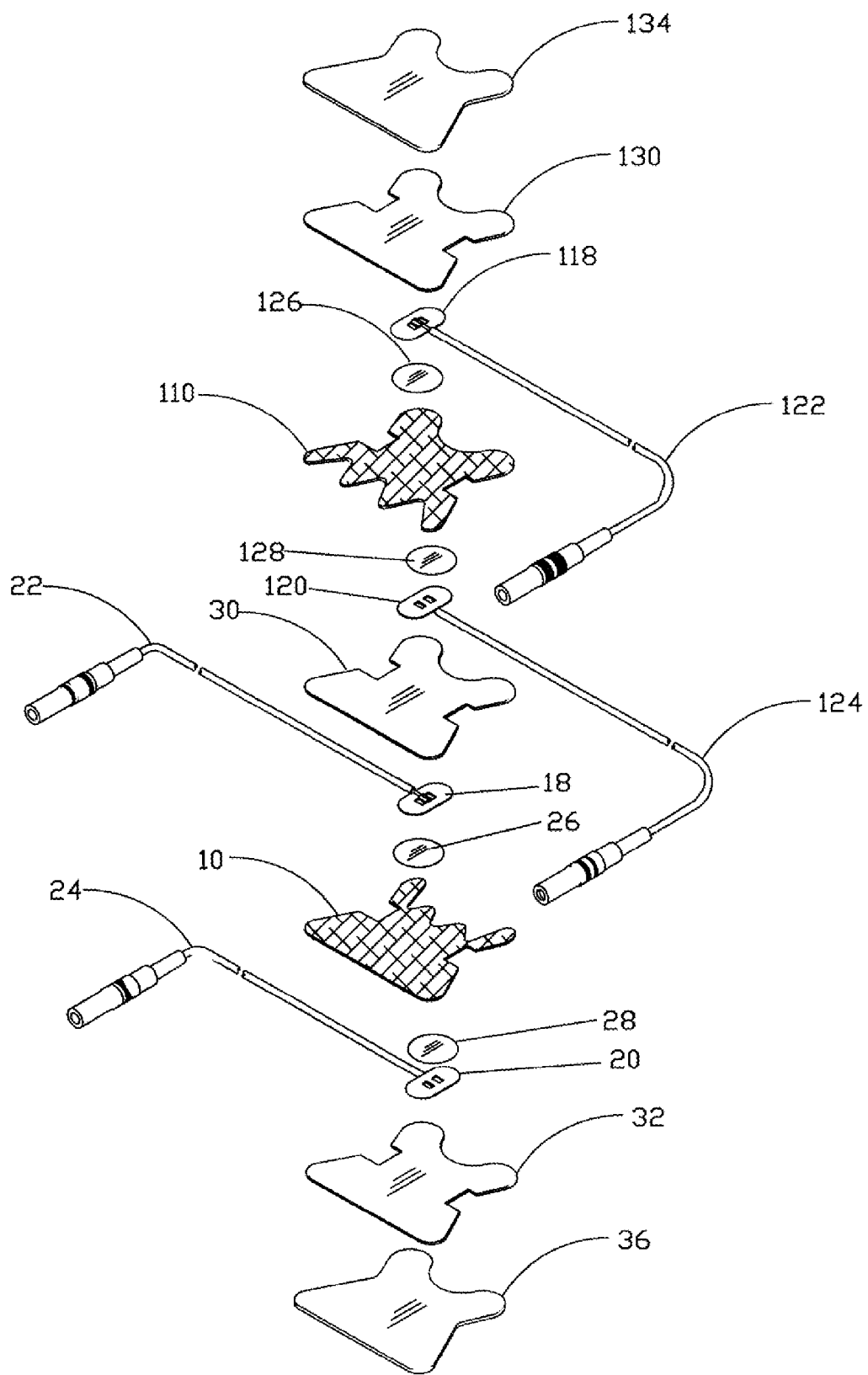
FIG. 3 illustrates generally an exploded view of an example of a polarized respiratory air temperature and pressure change sensor.
Figure 4:
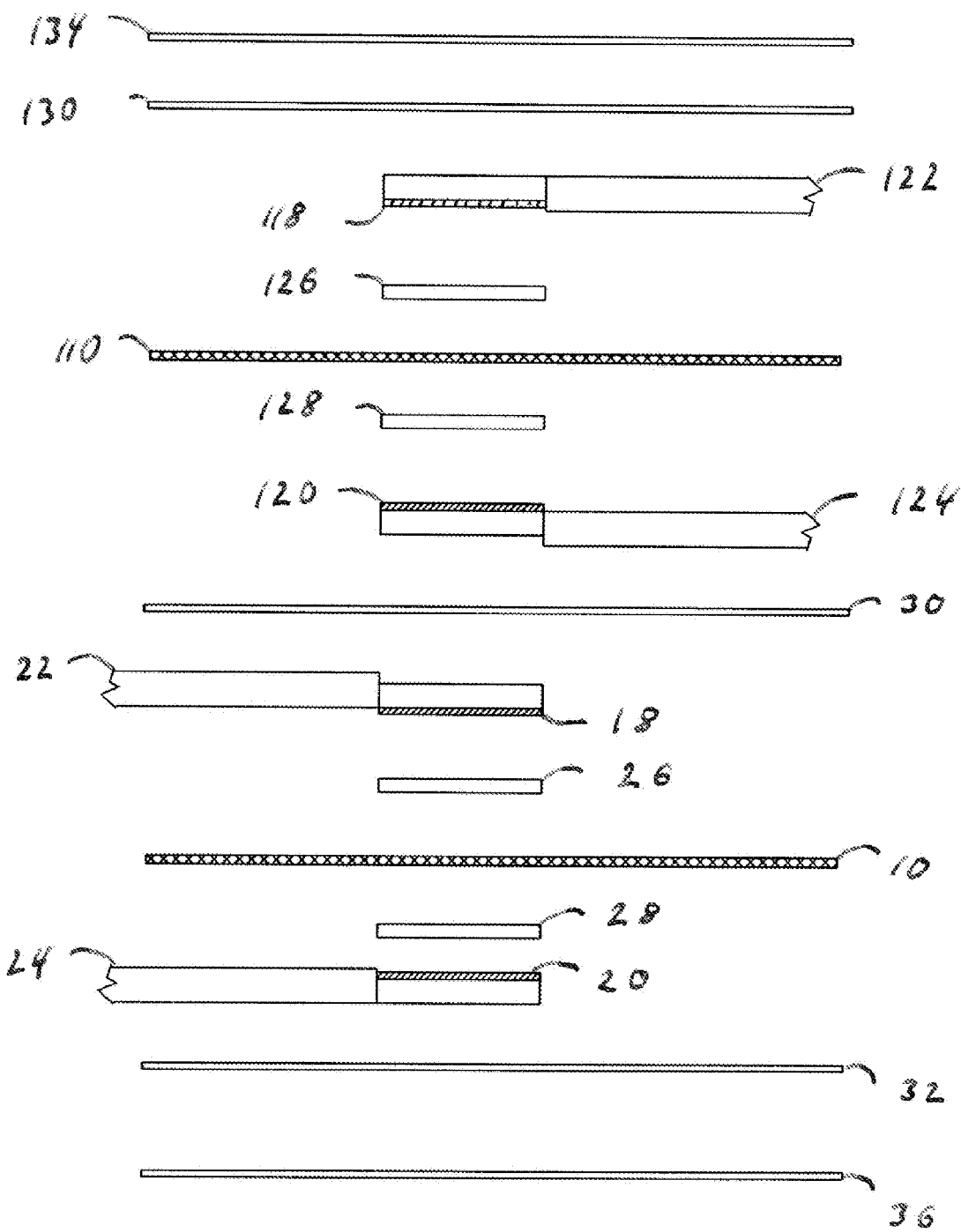
FIG. 4 illustrates generally an expanded edge view of an example of a polarized respiratory air temperature and pressure change sensor.

FIGS. 3-4 illustrate generally an exploded view and an expanded edge view of an example of a polarized respiratory air temperature and pressure change sensor.

Referring to FIGS. 3 and 4, there is illustrated generally an example sensor in an exploded perspective view and an exploded edge view. The sensor comprises as its active elements one pressure sensing PVDF film transducer 10 and one temperature sensing PVDF film transducer 110. The PVDF film transducers 10 and 110 include metallization layers on opposed major surfaces thereof represented by the cross-hatching thereon. The metallization layers serve to collect the charge produced by the PVDF film transducers due to respiratory air pressure changes impinging on the pressure sensing PVDF film transducer 10 and due to respiratory air temperature changes impinging on the temperature sensing PVDF film transducer 110.

Affixed to the opposed major surfaces of the center area of the pressure sensing PVDF film transducer 10 are conductive electrode tabs 18 and 20 that are crimped and/or soldered and/or otherwise affixed to the exposed ends of insulated lead wires 22 and 24, respectively.

Insulated lead wire 22 is preferably color coded black, marked with a black stripe or otherwise marked with a negative polarity-identifying feature because this wire becomes negative during operation when the side of the pressure sensing PVDF film transducer 10 is exposed to a respiratory air pressure change due to inhaling.

Insulated lead wire 24 is preferably color coded red, marked with a red stripe or otherwise marked positive polarity-identifying feature because this wire becomes positive during operation when the side of the PVDF film transducer 10 is exposed to a respiratory air pressure change due to inhaling.

The metallization layer of pressure sensing PVDF film transducer 10 that is connected to tab electrode 18 becomes negative when exposed to respiratory air pressure changes due to inhaling.

The metallization layer of pressure sensing PVDF film transducer 10 that is connected to tab electrode 18 becomes positive when exposed to respiratory air pressure changes due to exhaling.

The metallization layer of the pressure sensing PVDF film transducer 10 that is connected to tab electrode 20 becomes positive when exposed to respiratory air pressure changes due to inhaling.

The metallization layer of pressure sensing PVDF film transducer 10 that is connected to tab electrode 20 becomes negative when exposed to respiratory air pressure changes due to exhaling.

A conductive adhesive, such as that sold under the trademark ARclad® by Adhesives Research, Inc., can be used to assist contact between the conductive electrodes 18 and 20 and the metalized surfaces of the pressure sensing PVDF film transducer 10. This material comprises an adhesive that is laced with conductive carbon particles that serves as a bonding agent between the electrodes 18 and 20 with the metalized layers adhered to the PVDF film transducer. The ARclad® adhesive is represented in FIGS. 3 and 4 by references numerals 26, 28, 126 and 128.

First double-sided adhesive tape layer 32 cut to conform to the shape of the pressure sensing PVDF film transducer 10 and adhered to the opposed surfaces of the film layer 10 helping to secure the tab electrodes 20 and a portion of the wire lead 24 leading to the conductive tabs in place.

Second double-sided adhesive tape layer 30 cut to conform to the shape of the PVDF film transducer 10 and adhered to the opposed surfaces of the film layer 10 helping to secure the tab electrodes 18 and a portion of the wire lead 22 leading to the conductive tabs in place. The second double-sided adhesive tape layer 30 also acts as a buffering layer between the pressure (kinetic air molecule energy) sensing PVDF film transducer 10 and the temperature (thermal air molecule energy) sensing PVDF film transducer 110.

A third double-sided adhesive tape layer 130 is also cut to conform to the shape of the PVDF film temperature transducer 110 and is adhered to the surfaces of the film layer 110 opposite the second layer 30, helping to secure the tab electrodes 118 and 120 and a portion of the wire leads 122 and 124 leading to the conductive tabs in place.

Affixed to the opposed major surfaces of the center area of the temperature sensing PVDF film transducer 110 are conductive electrode tabs 118 and 120 that are crimped and/or soldered and/or otherwise affixed to the exposed ends of insulated lead wires 122 and 124, respectively.

Insulated lead wire 124 is preferably color coded black or marked with a black stripe or otherwise negative polarity-identifying feature because this wire becomes negative during operation when the side of the PVDF film transducer 110 is exposed to a respiratory air temperature change due to inhaling.

Insulated lead wire 122 is preferably color coded red or marked with a red stripe or otherwise positive polarity-identifying feature because this wire becomes negatively charged during operation when the temperature sensing PVDF film transducer 110 is exposed to a respiratory air temperature change due to inhaling.

The metallization layer of PVDF film temperature transducer 110 that is connected to tab electrode 120 becomes negative when exposed to respiratory air temperature cooling changes due to inhaling.

The metallization layer of PVDF film temperature transducer 110 that is connected to tab electrode 120 becomes positive when exposed to respiratory air temperature warming changes due to exhaling.

The metallization layer of PVDF film temperature transducer 110 that is connected to tab electrode 118 becomes positive when exposed to respiratory air temperature cooling changes due to inhaling.

The metallization layer of PVDF film temperature transducer 110 that is connected to tab electrode 118 becomes negative when exposed to respiratory air temperature warming changes due to exhaling.

Again, to assist contact between the conductive electrodes 118 and 120 and the metalized surfaces of the temperature sensing PVDF film transducer 110, a conductive adhesive, such as ARclad® adhesive, can be used. As mentioned, this material comprises an adhesive that is laced with conductive carbon particles that serve as a bonding agent between the electrodes 118 and 120 with the metalized layers adhered to the temperature sensing PVDF film transducer 110. The ARclad® adhesive is represented in FIGS. 3 and 4 by references numerals 126 and 128.

The illustrated sensor includes a first and second layer 134, 36 of polyurethane film. The layers are cut to be of generally the same shape as the pressure sensing PVDF film transducer 10 and the temperature sensing PVDF film transducer 110 but larger in size than the adhesive tape layers 30, 32 and 130. The first polyurethane plastic layer 134 is adhered to the exposed adhesive surface of the double-sided tape layer 130. Likewise, the second polyurethane plastic layer 36 is bonded to the exposed adhesive on the tape layer 32.

While polyurethane film is preferred for the outer layers 134 and 36, because it is heat-sealable and hydrophobic, other non-porous heat sealable plastic materials may also be used to encapsulate the PVDF film transducer and the distal ends of the lead wires.

Figure 5:
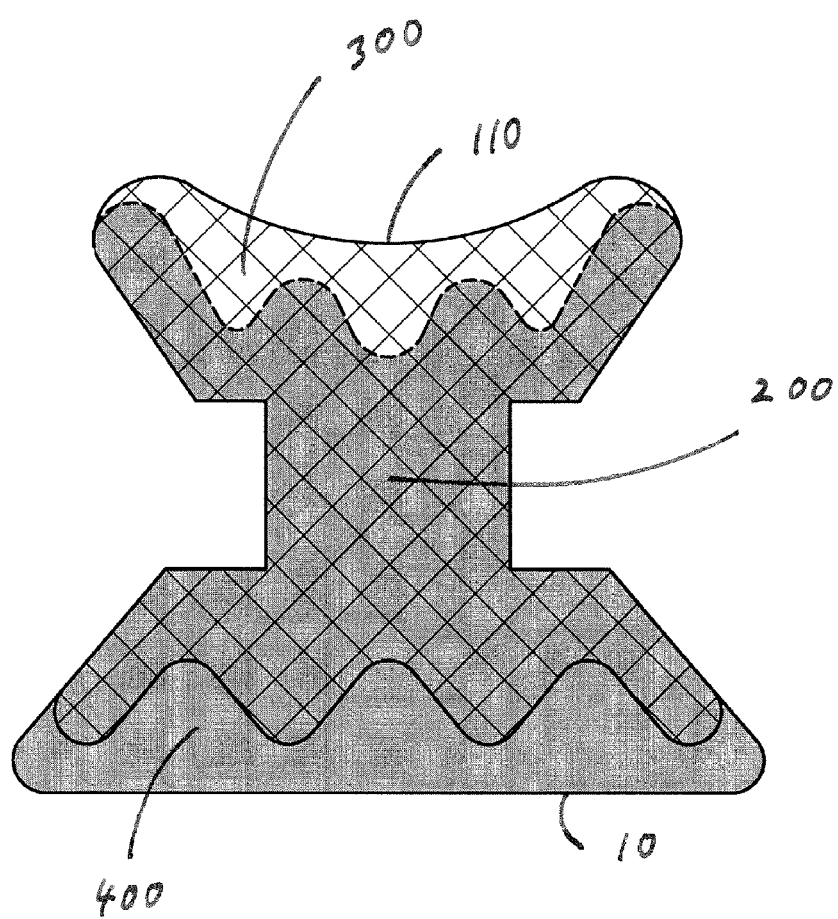
FIG. 5 illustrates generally a composite outline view showing an example of overlapping and non-overlapping areas between a temperature sensing PVDF film transducer and a pressure sensing PVDF film transducer according to one example of the present subject matter.

FIG. 5 illustrates generally a composite outline view showing an example of an overlapping and non-overlapping areas between a temperature sensing PVDF film transducer and a pressure sensing PVDF film transducer according to one example of the present subject matter. The nasal non-overlap area 300 exposes the inspired and expired air molecules more directly to the temperature detecting PVDF film transducer 110. The oral non-overlap area 400 exposes the inspired and expired air molecules more directly to the pressure detecting PVDF film transducer 10.

Figure 6:
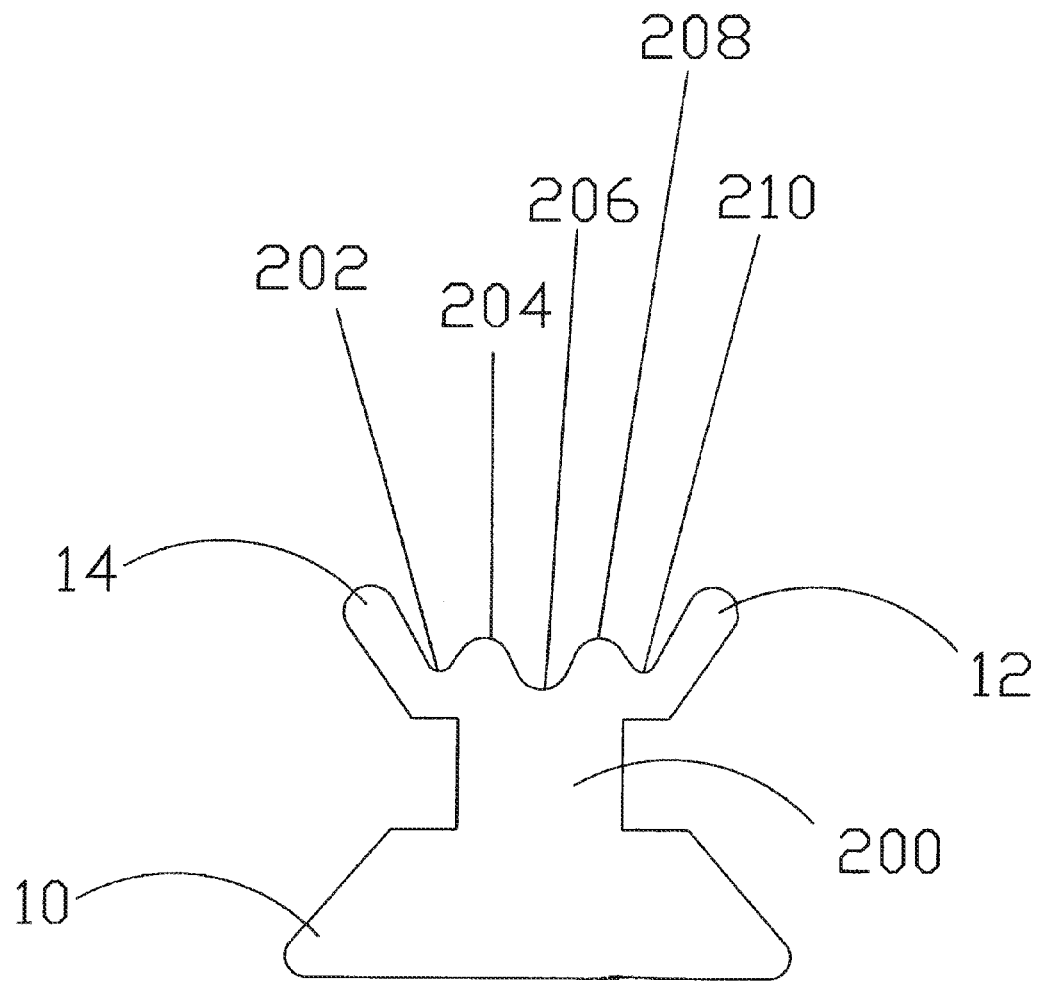
FIG. 6 illustrates generally an outline view of an example of a pressure sensing PVDF film transducer.

FIG. 6 illustrates generally an outline view of an example of a pressure sensing PVDF film transducer. Referring to FIG. 6, there is shown the single outline view of the pressure sensing PVDF film transducer 10 depicting the nasal cut out pattern. The nasal cutout pattern is bordered by a left lobe 14 and a right lobe 12. The nasal cutout center area consists of three cutout valleys 202, 206, 210 and two cutout peaks 204 and 208. The center area 200 is the common overlap for both the PVDF film transducers.

Figure 7:
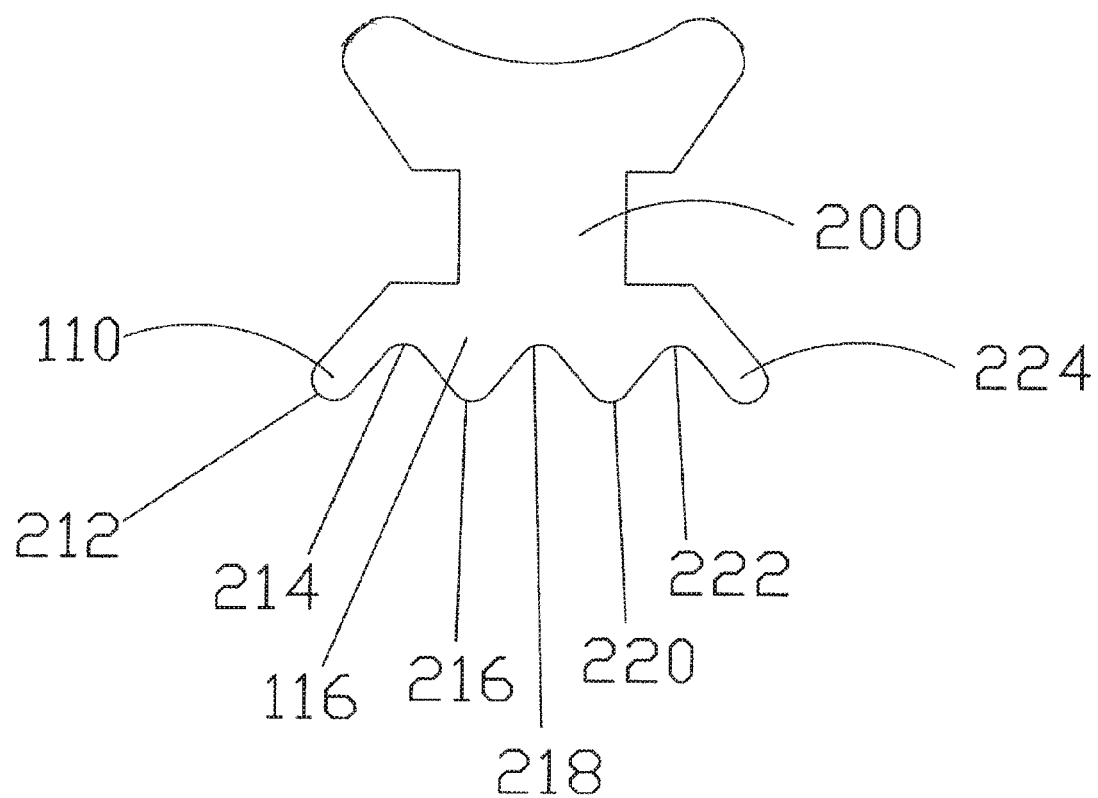
FIG. 7 illustrates generally an outline view of an example of a temperature sensing PVDF film transducer.

FIG. 7 illustrates generally an outline view of an example of a temperature sensing PVDF film transducer. Referring to FIG. 7, there is shown the single outline view of the temperature sensing PVDF film transducer 110 depicting the oral cut out pattern. The oral cutout pattern is bordered by a left lobe 212 and a right lobe 224. The oral cutout center area consists of three cutout peaks 214, 218, 222 and two cutout valleys 216 and 220. The center area 200 is the common overlap for both the PVDF film transducers.

For differently sized sensors, the nasal and oral cutout areas may be scaled linearly. Different sizes comprise of large adult, medium adult, and small adult, pediatric, infant and neonatal sensors.

In various examples, a polarized respiratory air temperature and pressure change sensor is provided for use in sleep monitoring equipment. The sensor comprises two differently shaped and sandwiched PVDF film transducers. In various examples, an energy-buffering layer 30 separates the two differently shaped PVDF film transducers. The two differently shaped PVDF film transducers, overlaid in a specified pattern creates two substantial PVDF film transducer non-overlap areas. One PVDF film transducer responds to thermal energy (temperature) and the other PVDF film transducer responds to the kinetic energy (pressure) of inhaled or exhaled air molecules. The pyroelectric signal (temperature) can be readily isolated from the piezoelectric signal (pressure) using signal processing technique embodied in the apparatus described in the afore-referenced provisional application of Peter Stasz, entitled "Method and Apparatus for Processing Respiratory Air Temperature and Pressure Change Transducer Signals".

In the simplest sense, temperature (thermal energy) is the result of the vibration of the individual molecule. The sum of the accelerated mass of the individual air molecules per transducer area generates the pressure (kinetic energy).

Various sensor examples incorporates both the temperature and the pressure sensing capabilities of PVDF film transducers into a single oral and nasal airflow sensor. The sensor senses inspired and expired oral and nasal air temperatures and pressures. One of the two PVDF film transducers converts pressure and the other converts temperature into an electrically equivalent and linear signal.

During operation in a typical application, such as in a sleep laboratory, a patient is fitted with a temperature and pressure sensor. In an example, the polarized temperature and pressure change sensor can be connected to a PSG machine. The sensor has been described herein for sleep scientists, sleep physicians and sleep technicians to see, detect and properly diagnose specific sleep disorders and diseases which may include abnormal respiratory events such as events occurring in the upper airway of the patient.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

The description of the various embodiments is merely exemplary in nature and, thus, variations that do not depart from the gist of the examples and detailed description herein are intended to be within the scope of the present disclosure. Such variations are not to be regarded as a departure from the spirit and scope of the present disclosure.

What is claimed is:

1. An apparatus for simultaneously detecting respiratory air temperature information and respiratory air pressure information from a patient, the apparatus comprising:
   a respiratory air temperature piezoelectric film sensor configured to detect respiratory air temperature information; and
   a respiratory air pressure piezoelectric film sensor configured to detect respiratory air pressure information;
   wherein at least a portion of the respiratory air temperature piezoelectric film sensor overlaps at least a portion of the respiratory air pressure piezoelectric film sensor, each of the respiratory air temperature piezoelectric film sensor and the respiratory air pressure piezoelectric film sensor including a non-overlap portion,
   wherein the non-overlap portion of the respiratory air temperature piezoelectric film sensor does not overlap any portion of the respiratory air pressure piezoelectric film sensor and the non-overlap portion of the respiratory air pressure piezoelectric film sensor does not overlap any portion of the respiratory air temperature piezoelectric film sensor,
   wherein the non-overlap portion of the respiratory air temperature piezoelectric film sensor is proximate a first end of the apparatus, and the non-overlap portion of the respiratory air pressure piezoelectric film sensor is proximate a second end of the apparatus, the second end substantially opposite to the first end.

2. The apparatus of claim 1, wherein the respiratory air temperature piezoelectric film sensor and the respiratory air pressure piezoelectric film sensor are included in a single sensor apparatus sized and shaped to be disposed on an upper lip of the patient.

3. The apparatus of claim 2, wherein the first end of the apparatus is exposed to nasal respiratory air flow and the second end of the apparatus is exposed to oral respiratory air flow.

4. The apparatus of claim 1, wherein the respiratory air temperature piezoelectric film sensor includes a respiratory air temperature polyvinylidene fluoride (PVDF) film sensor and the respiratory air pressure piezoelectric film sensor includes a respiratory air pressure PVDF film sensor.

5. The apparatus of claim 1, wherein each of the respiratory air temperature piezoelectric film sensor and the respiratory air pressure piezoelectric film sensor include a first major surface and a second major surface;
  wherein the respiratory air temperature piezoelectric film sensor includes a first electrode coupled to a the first major surface and a second electrode coupled to the second major surface; and
  wherein the respiratory air pressure piezoelectric film sensor includes a first electrode coupled to the first major surface and a second electrode coupled to the second major surface.

6. The apparatus of claim 5, wherein the first electrode of the respiratory air temperature piezoelectric film sensor is bonded to the first major surface of the respiratory air temperature piezoelectric film sensor using a conductive adhesive;
  wherein the second electrode of the respiratory air temperature piezoelectric film sensor is bonded to the second major surface of the respiratory air temperature piezoelectric film sensor using a conductive adhesive;
  wherein the first electrode of the respiratory air pressure piezoelectric film sensor is bonded to the first major surface of the respiratory air pressure piezoelectric film sensor using a conductive adhesive; and
  wherein the second electrode of the respiratory air pressure piezoelectric film sensor is bonded to the second major surface of the respiratory air pressure piezoelectric film sensor using a conductive adhesive.

7. The apparatus of claim 1, including:
  a first exterior layer overlying a first major surface of the respiratory air temperature piezoelectric film sensor opposite the respiratory air pressure piezoelectric film sensor; and
  a second exterior layer overlying a first major surface of the respiratory air pressure piezoelectric film sensor opposite the respiratory air temperature piezoelectric film sensor.

8. The apparatus of claim 1, including:
  a double sided adhesive tape layer disposed between the respiratory air temperature piezoelectric film sensor and the respiratory air pressure piezoelectric film sensor, the double sided adhesive tape layer configured to couple the respiratory air temperature piezoelectric film sensor to the respiratory air pressure piezoelectric film sensor and to isolate the respiratory air temperature piezoelectric film sensor from the respiratory air pressure piezoelectric film sensor.

9. The apparatus of claim 1, wherein the non-overlap portion of the respiratory air temperature piezoelectric film sensor is configured to be exposed to nasal respiration.

10. The apparatus of claim 1, wherein the non-overlap portion of the respiratory air pressure piezoelectric film sensor is configured to be exposed to oral respiration.

11. The apparatus of claim 1, wherein the respiratory air temperature piezoelectric film sensor is configured to provide information indicative of respiratory air temperature to an electronic signal processing circuit, the electronic signal processing circuit configured to produce a first signal output indicative of respiratory air temperature; and
  wherein the respiratory air pressure piezoelectric film sensor is configured to provide information indicative of respiratory air pressure to an electronic signal processing circuit, the electronic signal processing circuit configured to produce a second signal output indicative of respiratory air pressure.

12. The apparatus of claim 1, wherein the respiratory air temperature piezoelectric film sensor and the respiratory air pressure piezoelectric film sensor are configured to provide a rigid phase and polarity relationship between respiratory air temperature and respiratory air pressure.

13. A system comprising:
  a polarized respiratory air temperature and pressure piezoelectric film sensor, sized and shaped to be disposed on an upper lip of a patient, the polarized respiratory air temperature and pressure piezoelectric film sensor configured to receive oral and nasal respiration and to provide information indicative of respiratory air temperature and information indicative of respiratory air pressure to an electronic signal processing circuit, the polarized respiratory air temperature and pressure piezoelectric film sensor comprising:
    a respiratory air temperature piezoelectric film sensor configured to detect respiratory air temperature information;
    a respiratory air pressure piezoelectric film sensor configured to detect respiratory air pressure information;
    wherein at least a portion of the respiratory air temperature piezoelectric film sensor overlaps at least a portion of the respiratory air pressure piezoelectric film sensor, each of the respiratory air temperature piezoelectric film sensor and the respiratory air pressure piezoelectric film sensor including a non-overlap portion,
    wherein the non-overlap portion of the respiratory air temperature piezoelectric film sensor does not overlap any portion of the respiratory air pressure piezoelectric film sensor and the non-overlap portion of the respiratory air pressure piezoelectric film sensor does not overlap any portion of the respiratory air temperature piezoelectric film sensor,
    wherein the non-overlap portion of the respiratory air temperature piezoelectric film sensor is proximate a first end of the apparatus, and the non-overlap portion of the respiratory air pressure piezoelectric film sensor is proximate a second end of the apparatus, the second end substantially opposite to the first end; and
    wherein the non-overlap portion of the respiratory air temperature piezoelectric film sensor is configured to be exposed to nasal respiration, and the non-overlap portion of the respiratory air pressure piezoelectric film sensor is configured to be exposed to oral respiration;
  an electronic signal processing circuit configured to receive the information indicative of a respiratory air temperature and information indicative of a respiratory air pressure from the polarized respiratory air temperature and pressure piezoelectric film sensor, wherein the electronic signal processing circuit is configured to simultaneously process the received respiratory air temperature information and the received respiratory air pressure information to produce a first signal output indicative of respiratory air temperature and a second signal output indicative of respiratory air pressure; and
  a polysomnograph machine configured to receive the first signal output and the second signal output from the electronic signal processing circuit and to display the received respiratory air temperature information and the received respiratory air pressure information.

14. A method for simultaneously detecting respiratory air temperature information and respiratory air pressure information from a patient using an apparatus, comprising:

detecting respiratory air temperature information using a respiratory air temperature sensor including a first piezoelectric film;

detecting respiratory air pressure information using a respiratory air pressure sensor including a second piezoelectric film, at least a portion of the second piezoelectric film overlapping at least a portion of the first piezoelectric film, wherein the first piezoelectric film includes a first non-overlap portion proximate a first end of the apparatus and the second piezoelectric film includes a second non-overlap portion proximate a second end of the apparatus, the second end substantially opposite to the first end, wherein the first non-overlap portion of the first piezoelectric film does not overlap any portion of the second piezoelectric film and the second non-overlap portion of the second piezoelectric film sensor does not overlap any portion of the first piezoelectric film sensor.

15. The method of claim 14, including exposing the non-overlap portion of the first piezoelectric film sensor to nasal respiration; and exposing the non-overlap portion of the second piezoelectric film sensor to oral respiration.

16. The method of claim 14, wherein the detecting respiratory air temperature information and the detecting respiratory air pressure information includes using a single sensor apparatus sized and shaped to be disposed on an upper lip of the patient, the single sensor apparatus including the first piezoelectric film and the second piezoelectric film, wherein the first end of the apparatus is exposed to nasal respiratory air flow and the second end of the apparatus is exposed to oral respiratory air flow.

17. The method of claim 14, wherein the detecting respiratory air temperature information includes using a first polyvinylidene fluoride (PVDF) film; and wherein the detecting respiratory air pressure information includes using a second PVDF film.

18. The method of claim 14, including:

providing information indicative of respiratory air temperature to an electronic signal processing circuit, the electronic signal processing circuit configured to produce a first signal output indicative of respiratory air temperature; and providing information indicative of respiratory air pressure to an electronic signal processing circuit, the electronic signal processing circuit configured to produce a second signal output indicative of respiratory air pressure.

19. The method of claim 18, wherein the providing the information indicative of respiratory air temperature and respiratory air pressure include providing a rigid phase and polarity relationship between respiratory air temperature and respiratory air pressure.

20. The method of claim 18, wherein the providing the information indicative of respiratory air temperature includes using a first electrode coupled to a first major surface of first piezoelectric film and a second electrode coupled to a second major surface of the first piezoelectric film; and wherein the providing the information indicative of respiratory air pressure includes using a first electrode coupled to a first major surface of the second piezoelectric film and a second electrode coupled to a second major surface of the second piezoelectric film.

* * * * *